United States Patent
Zhang et al.

(10) Patent No.: US 9,857,348 B2
(45) Date of Patent: Jan. 2, 2018

(54) METHOD AND APPARATUS FOR SIMULTANEOUS ONLINE ASSAY OF NITRITES AND NITRATES IN WATER SAMPLES

(71) Applicant: Sichuan University, Chengdu (CN)

(72) Inventors: Xinshen Zhang, Chengdu (CN); Nan Li, Chengdu (CN); Xiaoping Jiang, Chengdu (CN)

(73) Assignee: Sichuan University, Chengdu (CN)

( * ) Notice: Subject to any disclaimer, the term of this patent is extended or adjusted under 35 U.S.C. 154(b) by 230 days.

(21) Appl. No.: 14/658,727

(22) Filed: Mar. 16, 2015

(65) Prior Publication Data

US 2015/0260701 A1   Sep. 17, 2015

(30) Foreign Application Priority Data

Mar. 17, 2014  (CN) .......................... 2014 1 0098759

(51) Int. Cl.
*G01N 33/18*   (2006.01)
(52) U.S. Cl.
CPC ................. *G01N 33/188* (2013.01)

(58) Field of Classification Search
None
See application file for complete search history.

(56) References Cited

U.S. PATENT DOCUMENTS

| | | | | |
|---|---|---|---|---|
| 5,462,660 A | * | 10/1995 | Singleton | ............... B01D 15/14 |
| | | | | 210/198.2 |
| 2006/0039827 A1 | * | 2/2006 | Zhang | .................... G01N 30/56 |
| | | | | 422/70 |
| 2009/0233370 A1 | * | 9/2009 | Zhang | ................. G01N 21/276 |
| | | | | 436/43 |

OTHER PUBLICATIONS

Ensafi et al., Simultaneous determination of nitrite and nitrate in various samples using flow injection with spectrophotometric detection, Analytica Chimica, Oct. 12, 1998.*

(Continued)

*Primary Examiner* — Jill Warden
*Assistant Examiner* — Julie Tavares
(74) *Attorney, Agent, or Firm* — Drinker Biddle & Reath LLP (57) ABSTRACT

The invention relates to an apparatus for simultaneous online assay of nitrites and nitrates in water samples with improved sensitivity and accuracy, enhanced capacity of anti-interference against salinity, reduced assay costs, and simplified operation.

8 Claims, 7 Drawing Sheets

(56) References Cited

OTHER PUBLICATIONS

Mikuska et al., Simultaneous determination of nitrite and nitrate in water by chemiluminescent flow-injection analysis, Analytica Chimica, Sep. 6, 2003.*
Feng et al., Simultaneous determination of nanomolar nitrite and nitrate in seawater using reverse flow injection analysis coupled with a long path length liquid waveguide capillary cell, Sep. 25, 2013.*
Electronic Supplementary Materials/Methods cited in Feng article, Simultaneous determination of nanomolar nitrite and nitrate in seawater using reverse flow injection analysis coupled with a long path length liquid waveguide capillary cell, Sep. 25, 2013.*
Hua et al., "Determination of Ammonia Nitrogen, Nitrate and Nitrite in Rivers by Dual System Ion Chromatography", *Tianjin Academy of Environmental Science, Tianjin*, pp. 75-81 (2013)—See Abstract.
Ji et al., "Simultaneous Determination of Nitrite and Nitrate in Meat Products by Suppressed Conductivity-ion Chromatography", *Food and Nutrition in China*, No. 10, pp. 50-52 (2010)—See Abstract.
Jiang et al., On-Line Determination of Nitrite and Nitrate in Sea-Water by Flow Injection Analysis, *Leather Science and Engineering*, vol. 22, No. 5, pp. 73-77 (2012)—See Abstract.

\* cited by examiner

METHOD AND APPARATUS FOR SIMULTANEOUS ONLINE ASSAY OF NITRITES AND NITRATES IN WATER SAMPLES

FIELD OF THE INVENTION

This invention relates to water sample assay, and in particular, to a method and apparatus for simultaneous online assay of nitrites and nitrates in water samples.

BACKGROUND OF THE INVENTION

Nitrites are widely used in various fields such as food industry, dye industry, and water deterioration inhibition. Nitrites can inhibit the growth and propagation of botulinum and prevent botulin poisoning, and the addition thereof in foods provides the foods with good color. However, upon absorption of nitrites by human body, normal hemoglobin can be converted into hemigiobin, and in turn loses its oxygen-carrying capacity. Also, nitrites can couple with secondary amines in human body or animal body, producing nitrosamines, which are strong carcinogens, and thus induce cancerization. The poisonous dose of nitrites is 0.3~0.5 g for adults, and the lethal dose is 1~3 g. According to the rules of Food and Agriculture Organization of the United Nations and World Health Organization (WHO), the permissible daily dose of nitrites is 0.2 mg/kg body weight. Nitrates per se are harmless to human body, but they might be converted into nitrites by nitrate-reducing bacteria in human body. Both nitrites and nitrates can lead to production of nitrosamines, which are strong carcinogens. Therefore, analysis and monitoring of the contents of nitrites and nitrates in water samples are necessary.

Methods known in the art for simultaneous assay of nitrites and nitrates include UV spectrophotometry, ion chromatography such as dual system ion chromatography or suppressed conductivity-ion chromatography, flow injection, or the like. Although these methods enable simultaneous assay of nitrites and nitrates, they have various disadvantages. The disadvantages of ion chromatography include: (1) It is high pressure ion chromatography and requires the use of a high pressure pump, making the apparatus inconvenient to carry, and thus is inapplicable for in situ assay. (2) It uses conductometry, and thus nitrites and nitrates, after anion chromatographic separation and before entering detection channel, have to pass through a suppressor or a suppressor column, which is extremely expensive and largely increases assay costs and complexity. (3) The service life of an anion chromatographic column is relatively short, which increases assay costs. (4) It has low detection sensitivity for nitrites and nitrates, with a detection limit of about 3 μg/l, for nitrites, and about 2 μg/l, for nitrates, based on N. (5) It has poor capacity against the interference of chloride ions, and thus cannot be applied in assay of nitrites and nitrates in seawater. The disadvantages of flow injection include: (1) Salinity interferes the accuracy of assay of nitrites and nitrates. (2) Operation is complicated, in that the apparatus needs to be adjusted manually for the assay of nitrates after that of nitrites. The disadvantages of UV spectrophotometry include: (1) It has low sensitivity. (2) Salinity interferes assay.

SUMMARY OF THE INVENTION

An object of the invention is to overcome the disadvantages of the prior art, and provide a method and apparatus for simultaneous online assay of nitrites and nitrates in water samples, in order to improve sensitivity and accuracy of assay, enhance capacity of anti-interference against salinity, reduce assay costs, and simplify operation.

The object of the invention is achieved by the provision of an apparatus for simultaneous online assay of nitrites and nitrates in water samples, and a method of using the same. The apparatus according to the invention can be operated at a low pressure (e.g. about $2~3\times10^5$ Pa).

In a first aspect, the invention provides an apparatus for simultaneous online assay of nitrites and nitrates in water samples, comprising a low pressure pump, a 6-way injection valve, a low pressure anion separation column, a mixer, a reduction column, a reactor, a sample vessel, an eluent vessel, a color developer solution vessel, and a waste liquid vessel, wherein the sample vessel is connected with a liquid inlet of the 6-way injection valve via the low pressure pump, the eluent vessel is connected with a liquid inlet of the 6-way injection valve via the low pressure pump, the color developer solution vessel is connected with an inlet of the mixer via the low pressure pump, the other inlet of the mixer is connected with a liquid outlet of the 6-way injection valve, the liquid inlet and the liquid outlet of the low pressure anion separation column are connected with a liquid outlet and a liquid inlet of the 6-way injection valve, respectively, the liquid inlet and the liquid outlet of the reduction column are connected with the outlet of the mixer and the inlet of the reactor, respectively, and a liquid outlet of the 6-way injection valve is connected with the waste liquid vessel, wherein all connections are effected by ducts, and the reduction column comprises a column body, filter membranes located at the liquid inlet and the liquid outlet of the column body, and column fillers in the inner cavity of the column body, wherein the column fillers are copperized cadmium particles, or a mixture of copperized cadmium powders and polystyrene-divinylbenzene resin.

In a second aspect, the invention provides an apparatus for simultaneous online assay of nitrites and nitrates in water samples, comprising a low pressure pump, a 6-way injection valve, a low pressure anion separation column, a mixer, a reduction column, a reactor, a sample loop, a sample vessel, an eluent vessel, a color developer solution vessel, and a waste liquid vessel, wherein the sample vessel is connected with a liquid inlet of the 6-way injection valve via the low pressure pump, the eluent vessel is connected with a liquid inlet of the 6-way injection valve via the low pressure pump, the color developer solution vessel is connected with an inlet of the mixer via the low pressure pump, the liquid inlet and the liquid outlet of the sample loop is connected with a liquid outlet and a liquid inlet of the 6-way injection valve, respectively, the liquid inlet of the low pressure anion separation column is connected with a liquid outlet of the 6-way injection valve, the liquid inlet and the liquid outlet of the reduction column are connected with the liquid outlet of the low pressure anion separation column and the other inlet of the mixer, respectively, the outlet of the mixer is connected with the inlet of the reactor, and a liquid outlet of the 6-way injection valve is connected with the waste liquid vessel, wherein all connections are effected by ducts, and the reduction column comprises a column body, filter membranes located at the liquid inlet and the liquid outlet of the column body, and column fillers in the inner cavity of the column body, wherein the column fillers are copperized cadmium particles, or a mixture of copperized cadmium powders and polystyrene-divinylbenzene resin.

Preferably, the column fillers in the low pressure anion separation column in the apparatus according to the first aspect or the second aspect of the invention are low pressure anion exchange resin, and an exemplary method for preparing the same comprises:

(1) adding the raw materials, styrene and divinylbenzene, and the catalyst, benzoyl peroxide, in a reaction vessel in a weight ratio of (400~1000):(40~100):1, and performing a polymerization reaction for 12~24 h at a temperature of 80~95° C. and under normal pressure, obtaining spherical styrene-divinylbenzene copolymer beads; and (2) adding the copolymer beads from step (1) in a reaction vessel, followed by addition of a 70~72 wt. % alcoholic solution of chloromethyl methyl ether in a ratio of weight of copolymer beads (kg):volume of alcoholic solution of chloromethyl methyl ether (L)=1:4~1:5 to react for 8~10 h at a temperature of 45~50° C. for chloromethylation, then adding a 30~33 wt. % aqueous solution of trimethylamine in a ration of weight of copolymer beads (kg):volume of aqueous solution of trimethylamine (L) 1:4~1:5 to react for 12~24 h at a temperature of 35~40° C. for amination, obtaining anion exchange resin beads with quaternary ammonium functional groups.

Preferably, the column fillers in the reduction column in the apparatus according to the first aspect or the second aspect of the invention are copperized cadmium particles, in which the cadmium particles have a particle size of 0.5~1.0 mm and the thickness of copper layer is 0.05~0.1 mm, and an exemplary method for preparing the same comprises: making cadmium particles having a particle size of 0.5~1.0 mm from cadmium blocks, filling the cadmium particles into a reduction column, and then flushing them with a mixed aqueous solution of copper sulfate and EDTA, in which the concentration of copper sulfate is 6.14~6.64 g/L, and that of EDTA is 1438~14.88 g/L, at a flow rate of 0.8~1.2 mL/min for 20~30 min to obtain the product.

Preferably, the column fillers in the reduction column in the apparatus according to the first aspect or the second aspect of the invention are a mixture of copperized cadmium powders and polystyrene-divinylbenzene resin in a weight ratio of 1:1~1:2, and an exemplary method for preparing the same comprises: adding cadmium powders having a particle size of 75~150 μm in a reaction vessel, then adding a mixed aqueous solution of copper sulfate and EDTA, in which the concentration of copper sulfate is 6.14~6.64 g/L and that of EDTA is 1438~44.88 g/L, at a ratio of 18~20 mL solution per 1 g cadmium powders, reacting for 5-10 min with stirring, and after filtration, mixing the resulting copperized cadmium powders with styrene-divinylbenzene resin having a particle size of 100~200 μm at a weight ratio of 1:1~1:2 to obtain the product.

Preferably, the reduction column has an inner diameter of 3~4 mm and a length of 40~50 mm.

The apparatus according to the first aspect or the second aspect of the invention is useful for processing samples in simultaneous online assay of nitrites and nitrates in water samples. Preferably, the apparatus further comprises an optical flow cell, an optical detector, and a computer system, in order to accomplish simultaneous online assay of nitrites and nitrates in water samples.

In a third aspect, the invention provides a method for simultaneous online assay of nitrites and nitrates in water samples, using the apparatus according to the first aspect or the second aspect of the invention for processing samples, and analyzing via testing components, which include an optical flow cell, an optical detector, and a computer system.

When using an apparatus according to the first aspect of the invention, the method includes the following steps:

(1) setting the apparatus in injection state, wherein an eluent enters the mixer via the low pressure pump and the 6-way injection valve, a color developer solution enters the mixer via the low pressure pump, and they form a mixed solution in the mixer; the mixed solution enters the optical flow cell via the reduction column and the reactor, and the signal produced by the optical detector is transferred to the computer system for processing to obtain a baseline; and simultaneously, a test sample enters the low pressure anion separation column from the liquid inlet thereof via the low pressure pump and the 6-way injection valve, and saturates the low pressure anion separation column;

(2) switching the apparatus to analytical state, wherein the color developer solution enters the mixer via the low pressure pump, and the eluent enters the low pressure anion separation column from the liquid outlet thereof via the low pressure pump and the 6-way injection valve, to backwash the nitrites and nitrates in the low pressure anion separation column; driven by the eluent, the nitrites, which have low affinity to the column fillers, and the nitrates, which have high affinity to the column fillers, successively, flow out of the low pressure anion separation column and enter the mixer, where the nitrites are mixed with the color developer solution and then enter the reactor via the reduction column to accomplish a color development reaction forming a reaction solution, while the nitrates are mixed with the color developer solution and then enter the reduction column to be reduced to nitrites, which, in the form of a mixed solution with the color developer solution, enter the reactor to accomplish a color development reaction forming a reaction solution; the two reaction solutions enter, successively, the optical flow cell; and the signal produced by the optical detector is transferred to the computer system for processing to obtain a spectrogram of the nitrites and the nitrates;

(3) obtaining a spectrogram for each of a series of standard samples, in which the concentrations of nitrites and nitrates are known, by replacing the test sample with each of the standard samples and repeating the above steps (1) and (2); and plotting working curves, using the concentrations in the standard samples on the X-axis, and the peak heights in the spectrograms of the standard samples on the Y-axis; and (4) calculating the concentrations of nitrites and nitrates in the test sample by substituting the peak heights in the spectrogram of the test sample into the regression equations of the working curves of step (3).

When using an apparatus according to the second aspect of the invention, the method includes the following steps:

(1) setting the apparatus in injection state, wherein an eluent enters the mixer via the low pressure pump, the 6-way injection valve, the low pressure anion separation column and the reduction column successively, a color developer solution enters the mixer via the low pressure pump, and they form a mixed solution in the mixer; the mixed solution enters the optical flow cell via the reactor, and the signal produced by the optical detector is transferred to the computer system for processing to obtain a baseline; and simultaneously, a test sample enters the sample loop via the low pressure pump and the 6-way injection valve, and fills the sample loop;

(2) switching the apparatus to analytical state, wherein the color developer solution enters the mixer via the low pressure pump, and the eluent enters the sample loop via the low pressure pump and the 6-way injection valve and brings the test sample in the sample loop to the low pressure anion separation column via the 6-way injection valve; driven by the eluent, the nitrites, which have low affinity to the column fillers, and the nitrates, which have high affinity to the column fillers, successively, flow out of the low pressure anion separation column and enter the reduction column; the nitrites enter the mixer via the reduction column and are mixed with the color developer solution, and then enter the reactor, where a color development reaction occurs to form a reaction solution; the nitrates are reduced to nitrites in the reduction column, the resulting nitrites enter the mixer and are mixed with the color developer solution, and then enter the reactor, where a color development reaction occurs to form a reaction solution; the two reaction solutions enter, successively, the optical flow cell; and the signal produced by the optical detector is transferred to the computer system for processing to obtain a spectrogram of the nitrites and the nitrates;

(3) obtaining a spectrogram for each of a series of standard samples, in which the concentrations of nitrites and nitrates are known, by replacing the test sample with each of the standard samples and repeating the above steps (1) and (2); and plotting working curves, using the concentrations in the standard samples on the X-axis, and the peak heights in the spectrograms of the standard samples on the Y-axis; and (4) calculating the concentrations of nitrites and nitrates in the test samples by substituting the peak heights in the spectrogram of the test sample into the regression equations of the working curves of step (3).

Preferably, the volume of the sample loop is 150~250 μL.

Preferably, the color developer solution is prepared by mixing a sulfonamide solution, hydrochloric acid, and a N-(1-naphthyl)ethylenediamine dihydrochloride solution, and in the color developer solution, the concentration of sulfonamide is 2.00~2.50 g/L, the concentration of hydrochloric acid is 0.6~0.8 mol/L, and the concentration of N-(1-naphthyl)ethylenediamine dihydrochloride is 0.200~0.250 g/L.

Preferably, the eluent is a mixed aqueous solution of sodium chloride and ammonium chloride, wherein the concentration of sodium chloride is 1.50~3.09 wt. % and the concentration of ammonium chloride is 1.50~3.00 wt. %.

Preferably, the detection wavelength of the optical detector is 530 nm.

The invention provides a new sample processing apparatus and a new method for simultaneous online assay of nitrites and nitrates in water samples, having the following beneficial effects:

1. Simultaneous online assay of nitrites and nitrates in water samples is enabled with high assay sensitivity. Experiments (see Example 5) show detection limits as low as 0.03 μg/L for nitrites and 0.04 μg/L for nitrates, respectively, based on N.

2. Operation is at low pressure. Use of an expensive suppressor or suppressor column is avoided, and a low pressure anion separation column with complete exchange capacity (having a service life longer than that of a surface anion separation column currently employed in high pressure ion chromatography) is employed, thus lowering assay costs.

3. High anti-interference capacity is achieved. Experiments (see Example 9) show detection limits of 0.47 μg/L for nitrites and 0.34 μg/L for nitrates, respectively, based on N, in assay of an seawater sample. Therefore, they are applicable for simultaneous online assay of nitrites and nitrates in seawater.

4. High accuracy is achieved. Experiments (see Examples 4 and 8) show relative standard deviations of the peak heights of nitrites and nitrates in the spectrograms as low as 1.17% and 1.34%, respectively.

5. The volume and weight of apparatus are significantly reduced, in comparison to the available high pressure ion chromatography.

6. Higher simultaneity and simpler operation are achieved, in comparison to flow injection. Assay of nitrates can be effected after that of nitrites without manual adjustment.

The symbols in the drawings are as follows: 1—low pressure pump, 2—6-way injection valve, 3—low pressure anion separation column, 4—computer system, 5—optical detector, 6—mixer, 7—reduction column, 7-1—fixed hub, 7-2—column tube, 7-3 column fillers, 7-4—filter membrane, 7-5—plug, 7-6—duct, 8—reactor, 9—optical flow cell, 10—sample loop, 11—sample vessel, 12—eluent vessel, 13—color developer solution vessel, 14—waste liquid vessel, 15—testing components, $S_1$—test sample, $S_2$—standard sample, E—eluent, R—color developer solution, W—waste liquid.

DETAILED DESCRIPTION OF THE INVENTION

The invention will be further illustrated by way of examples below. These examples are only illustrations of the invention and do not limit it. The chemical reagents such as sodium nitrite, sodium nitrate, sulfonamide, hydrochloric acid, N-(1-naphthyl)ethylenediamine dihydrochloride, sodium chloride, ammonium chloride, are all analytically pure. The concentrations of nitrites and nitrates mentioned in the examples are all based on N.

Example 1

Preparation of Low Pressure Anion Exchange Resin (1) The raw materials, styrene and divinylbenzene, and the catalyst, benzoyl peroxide, were added in a reaction vessel in a weight ratio of 600:60:1, and a polymerization reaction was performed for 15 h at a temperature of 90° C. and under normal pressure, obtaining spherical styrene-divinylbenzene copolymer beads.

(2) The copolymer beads from step (1) were added in a reaction vessel, and a 70 wt. % alcoholic solution of chloromethyl methyl ether was added in a ratio of weight of copolymer beads (kg):volume of alcoholic solution of chloromethyl methyl ether (L)=1:4 to react for 8 h at a temperature of 50° C. for chloromethylation. Then a 30 wt. % aqueous solution of trimethylamine was added in a ratio of weight of copolymer beads (kg):volume of aqueous solution of trimethylamine (L)=1:4 to react for 12 h at a temperature of 40° C. for amination, obtaining anion exchange resin beads with quaternary ammonium functional groups.

Example 2

Structure of Reduction Column and Preparation of Column Fillers

Figure 1:
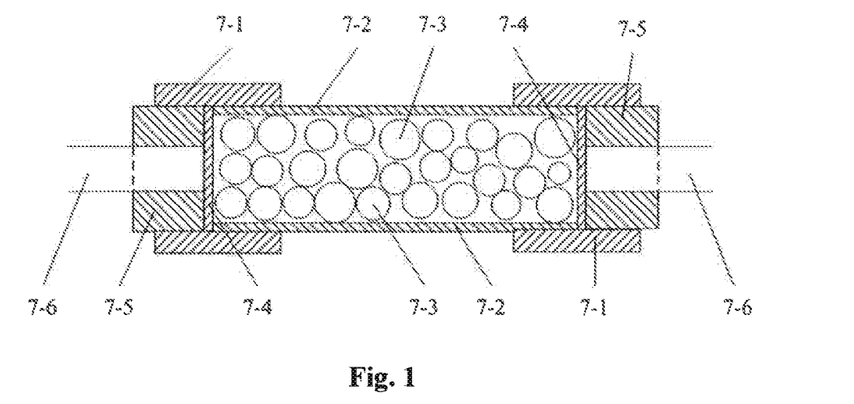
FIG. 1 is a structural schematic illustration of the reduction column in the apparatus of the invention.

The reduction column in this example has an inner diameter of 3 mm and a column length of 40 mm. The structure thereof is shown in FIG. 1. It mainly comprises a column body, filter membranes 7-4 located at the liquid inlet and the liquid outlet of the column body, and column fillers in the inner cavity of the column body. The column body comprises a column tube 7-2, plugs 7-5, fixed hubs 7-1, and ducts 7-6. The plugs 7-5 are located on the outside of the filter membranes 7-4, and have center holes for the insertion of the ducts 7-6. The fixed hubs 7-1 are located at the junctions of the plugs 7-5 and the column tube 7-2, for fixing the plugs 7-5 on the column tube 7-2. The filter membranes 7-4 are made of ninon, and are mounted between the column tube 7-2 and the plugs 7-5 at both ends. The column tube 7-2 is made of glass, and is filled with the column fillers 7-3. The column fillers 7-3 are copperized cadmium particles, in which the cadmium particles have a particle size of 0.5 mm and the thickness of copper layer is 0.05 mm. Both the fixing plugs 7-5 and the fixed hubs 7-1 are made of silicon rubber, and the ducts 7-6 are polytetrafluoroethylene ducts.

The column fillers 7-3 were prepared as follows. Cadmium blocks were hammered to pieces having a thickness of 0.5~1.0 mm, which were then cut into particles having a particle size of 0.5~1.0 mm. The cadmium particles were filled into the column tube 7-2, and then flushed with a mixed aqueous solution of copper sulfate and EDTA, in which the concentration of copper sulfate was 6.64 g/L, and that of EDTA was 14.88 g/L, at a flow rate of 0.8~1.2 mL/min for 30 min to obtain the product.

Example 3

Figure 2:
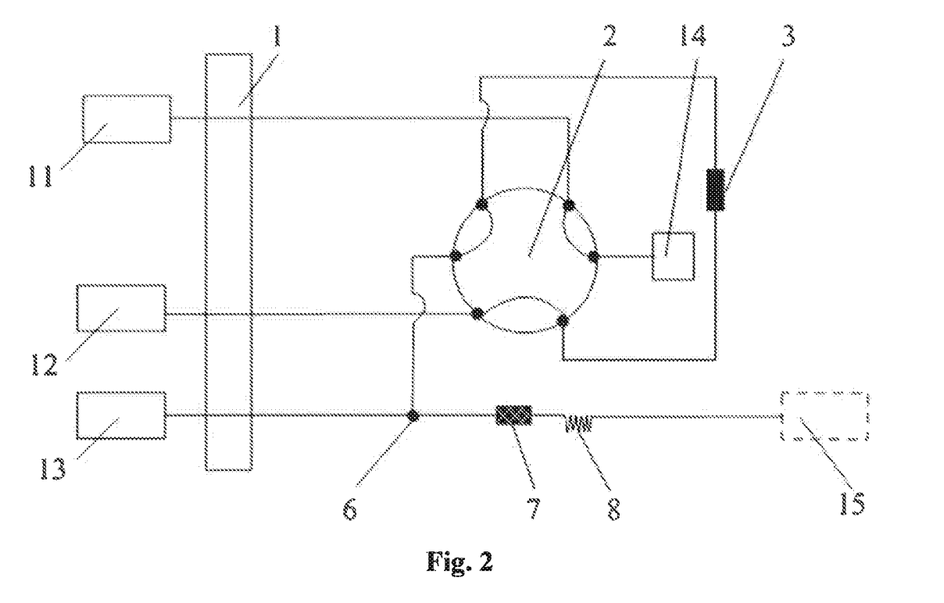
FIG. 2 is a structural schematic illustration of the apparatus according to the first aspect of the invention.

Apparatus (I) for Simultaneous Online Assay of Nitrites and Nitrates in Water Samples The structure of Apparatus (I) is shown in FIG. 2. It comprises a low pressure pump 1, a 6-way injection valve 2, a low pressure anion separation column 3, a mixer 6, a reduction column 7, a reactor 8, a sample vessel 11, an eluent vessel 12, a color developer solution vessel 13, and a waste liquid vessel 14. The reactor 8 is of a coil structure, and was made by winding a polytetrafluoroethylene tube having a length of 3.0 m and an inner diameter of 0.5 mm. The low pressure anion separation column 3 has an inner diameter of 5 mm and a column length of 40 mm, and the column fillers therein were prepared according to Example 1. The reduction column 7 is the one described in Example 2. The working pressure of the low pressure pump 1 is $2 \sim 3 \times 10^5$ Pa. The components of Apparatus (I) are assembled in the following way.

The sample vessel 11 is connected with a liquid inlet of the 6-way injection valve 2 via the low pressure pump 1. The eluent vessel 12 is connected with a liquid inlet of the 6-way injection valve 2 via the low pressure pump 1. The color developer solution vessel 13 is connected with an inlet of the mixer 6 via the low pressure pump 1. The other inlet of the mixer 6 is connected with a liquid outlet of the 6-way injection valve 2. The liquid inlet and the liquid outlet of the low pressure anion separation column 3 are connected with a liquid outlet and a liquid inlet of the 6-way injection valve 2, respectively. The liquid inlet and the liquid outlet of the reduction column 7 are connected with the outlet of the mixer 6 and the inlet of the reactor 8, respectively. A liquid outlet of the 6-way injection valve 2 is connected with the waste liquid vessel 14. All connections are effected by ducts.

Example 4

Accuracy of Assay Using Apparatus (I)

A standard sample was assayed using Apparatus (I) described in Example 3 to evaluate the accuracy of the assay. The steps were as follows:

1. A mixed solution, as standard sample $S_2$, was prepared with deionized water, sodium nitrate, and sodium nitrite, having a nitrate concentration of 20 μg/L and a nitrite concentration of 5 μg/L.

2. Color developer solution R was prepared as follows. 2.50 g sulfonamide was added in a 1000 mL volumetric flask, and 600 ml deionized water was added. Then 100 mL 8 mol/L hydrochloric acid was added without waiting for complete dissolution of the sulfonamide. After shaking, 0.250 g N-(1-naphthyl)ethylenediamine dihydrochloride was added and dissolved, and then deionized water was added to the volume 1000 mL, obtaining the product.

3. A mixed aqueous solution having a sodium chloride concentration of 1.50 wt. % and an ammonium chloride concentration of 1.50 wt. % was prepared, as eluent E.

4. Assay was carried out and a spectrogram of the standard sample was mapped.

Figure 3:
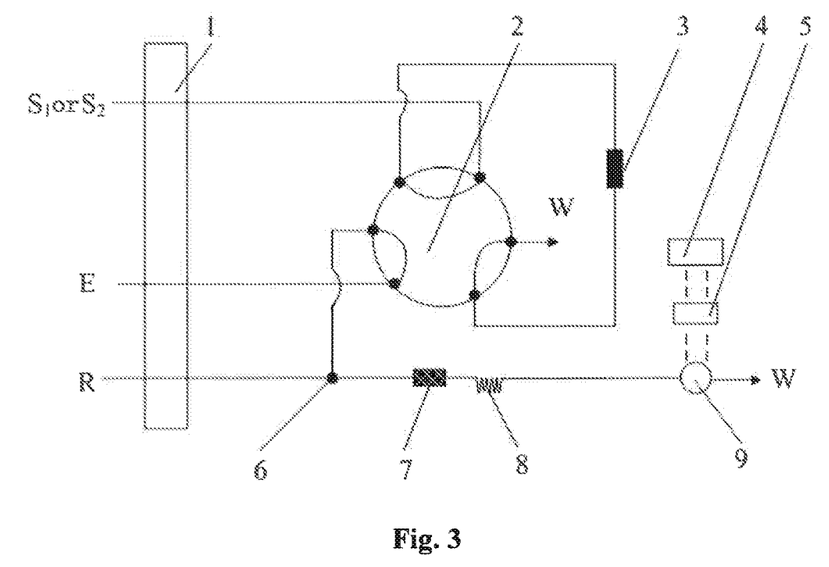
FIG. 3 is a schematic illustration of the flow path of the apparatus according to the first aspect of the invention in injection state when used in the method for simultaneous online assay of nitrites and nitrates in water samples.
Figure 4:
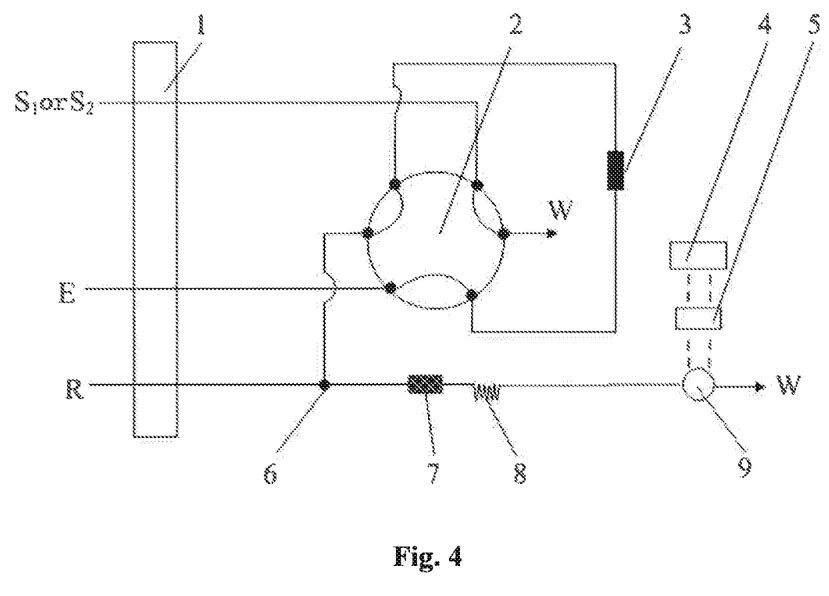
FIG. 4 is a schematic illustration of the flow path of the apparatus according to the first aspect of the invention in analytical state when used in the method for simultaneous online assay method of nitrites and nitrates in water samples.

The assay was carried out using Apparatus (I) described in Example 3 (further comprising testing components 15, comprising an optical flow cell 9, an optical detector 5 and a computer system 4), and the flow paths as shown in FIG. 3 and FIG. 4 were employed. In the low pressure pump 1, the flow rate in the pump line of standard sample $S_2$ was 0.2~0.4 mL/min, the flow rate in the pump line of color developer solution R was 0.8~1.2 mL/mm, the flow rate in the pump line of eluent E was 0.8~1.2 mL/min, and the working pressure was $2 \sim 3 \times 10^5$ Pa. The standard sample $S_2$, the eluent E and the color developer solution R were filled in the sample vessel 11, the eluent vessel 12, and the color developer solution vessel 13, respectively. The optical path of the optical flow cell 9 was 28 mm, and the detection wavelength of the optical detector 5 was 530 nm. The computer system 4 was a conventional computer installed with HW-2000 chromatography workstation (Shanghai Qianpu Software Company Ltd.).

The assay included the following steps:

(1) Baseline mapping. Apparatus (I) was set in injection state, and the flow path is shown in FIG. 3. The apparatus was turned on. Driven by the low pressure pump 1, eluent E entered the mixer 6 via the low pressure pump 1 and the 6-way injection valve 2, color developer solution R entered the mixer 6 via the low pressure pump 1, and they were mixed and formed a mixed solution in the mixer 6. The mixed solution entered the optical flow cell 9 via the reduction column 7 and the reactor 8, and the signal produced by the optical detector 5 was transferred to the computer system 4 for processing to obtain a baseline. Simultaneously, standard sample $S_2$ entered the low pressure anion separation column 3 from the liquid inlet thereof via the low pressure pump 1 and the 6-way injection valve 2, and saturated the low pressure anion separation 3. Excess standard sample $S_2$ was discharged into the waste liquid vessel 14 via a waste liquid outlet.

(2) Mapping of the spectrogram of the standard sample. Apparatus (I) was switched to analytical state, and the flow path is shown in FIG. 4. Driven by the low pressure pump 1, color developer solution R entered the mixer 6 via the low pressure pump 1, and eluent E entered the low pressure anion separation column 3 from the liquid outlet thereof via the low pressure pump 1 and the 6-way injection valve 2, to backwash the nitrites and nitrates in the low pressure anion separation column 3. Driven by eluent E, the nitrites, which had low affinity to the column fillers, and the nitrates, which had high affinity to the column fillers, successively, flowed out of the low pressure anion separation column 3 and entered the mixer 6, where the nitrites were mixed with color developer solution R and then entered the reactor 8 via the reduction column 7 to accomplish a color development reaction forming a reaction solution, while the nitrates were mixed with color developer solution R and then entered the reduction column 7 to be reduced to nitrites, which, in the form of a mixed solution with color developer solution R, entered the reactor 8 to accomplish a color development reaction forming a reaction solution. The two reaction solutions entered, successively, the optical flow cell 9. The signal produced by the optical detector was transferred to the computer system 4 for processing to obtain a spectrogram of nitrites and nitrates in standard sample $S_2$.

Figure 5:
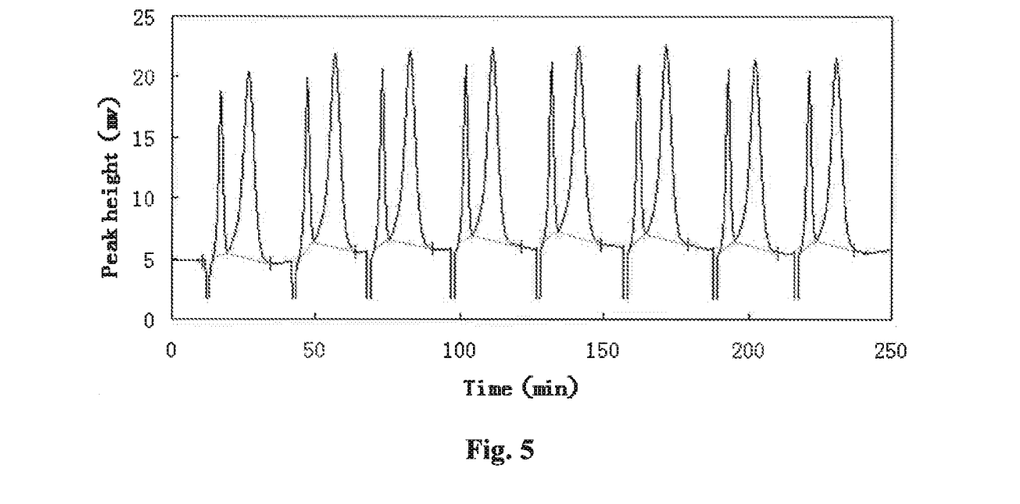
FIG. 5 is the spectrogram of accuracy of the standard sample obtained in Example 4.

The above steps (1) and (2) were repeated for 8 times, and a spectrogram as shown in FIG. 5 was obtained, wherein the relative standard deviation of the peak heights of nitrites and nitrates were 1.51% and 1.34%, respectively, demonstrating good accuracy of the assay of the invention.

Example 5

Assay of Water Samples Using Apparatus (I)

Water samples (commercially available pure drinking water) were assayed using Apparatus (I) described in Example 3. A total of 3 samples (test sample 1#, test sample 2#, and test sample 3#) were assayed with the following steps:

1. Standard samples 1# to 5# were prepared with deionized water, sodium nitrate, and sodium nitrite, wherein standard sample 1# was deionized water; standard sample 2# was a mixed solution in which the concentrations of nitrites and nitrates were 0.1 µg/l, and 1.0 µg/L, respectively; standard sample 3# was a mixed solution in which the concentrations of nitrites and nitrates were 0.2 µg/L and 2.0 µg/L, respectively; standard sample 4# was a mixed solution in which the concentrations of nitrites and nitrates were 0.5 µg/L and 5.0 µg/L, respectively; and standard sample 5# was a mixed solution in which the concentrations of nitrites and nitrates were 2.0 µg/L and 10.0 µg/L, respectively.

2. Color developer solution R was prepared as follows. 2.00 g sulfonamide was added in a 1000 mL volumetric flask, and about 600 ml deionized water was added. Then, 100 mL 6 mol/L hydrochloric acid was added without waiting for complete dissolution of the sulfonamide. After shaking, 0.200 g N-(1-naphthyl)ethylenediamine dihydrochloride was added and dissolved, and then deionized water was added to the volume 1000 mL, obtaining the product.

3. A mixed aqueous solution having a sodium chloride concentration of 3.09 wt. % and an ammonium chloride concentration of 3.00 wt. % was prepared, as eluent E.

4. Assay was carried out and spectrograms of the standard samples were mapped.

The assay was carried out according to step 4 in Example 4, with steps (1) and (2) being performed using test sample 1#, test sample 2#, test sample 3#, standard sample 1#, standard sample 2#, standard sample 3#, standard sample 4#, and standard sample 5#, respectively, instead of standard sample $S_2$ in Example 4, obtaining a spectrogram of each of the test samples and the standard samples.

5. Working curves were plotted using the concentrations (µg/L) of standard samples 1#-5# on the X-axis, and the peak heights (mV) in the spectrograms of standard samples 1#-5# on the Y-axis. The resulting working curves of nitrites and nitrates were shown in FIG. 10 and FIG. 11, respectively.

Figure 10:
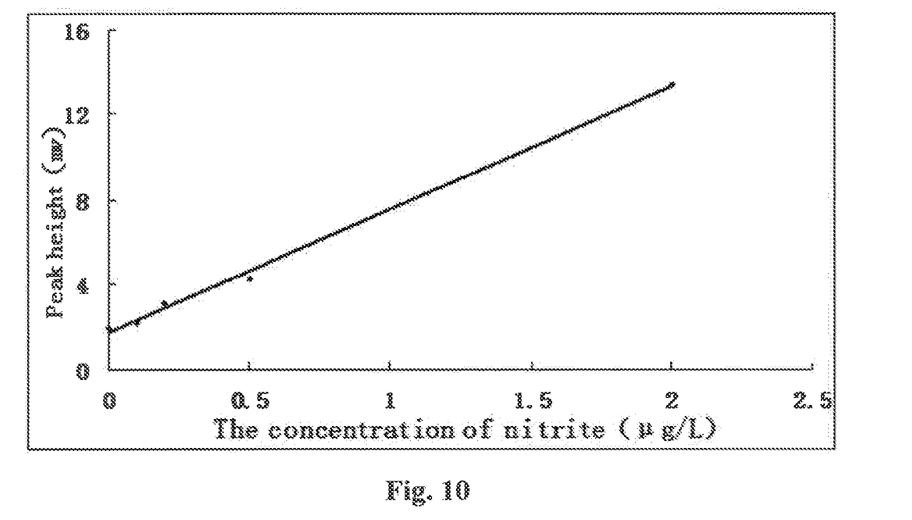
FIG. 10 is the working curve of nitrites obtained in Example 5.
Figure 11:
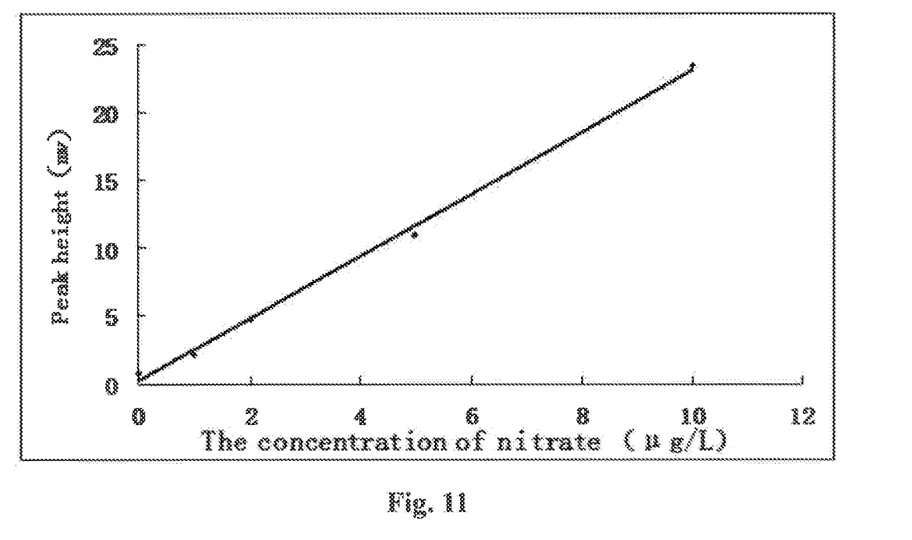
FIG. 11 is the working curve of nitrates obtained in Example 5.

6. Regression equations were established. The regression equation obtained from the working curve of nitrites as shown in FIG. 10 was H=5.7919C+1.7336, wherein H represented peak height (mV) and C represented concentration (µg/L) of nitrites in standard samples, and the correlation coefficient R was 0.999. The regression equation obtained from the working curve of nitrates as shown in FIG. 11 was H=2.2957C+0.1755, wherein H, C and R were as defined above for FIG. 10. The baseline noise in the assay was 0.32 mV, and it was calculated that the detection limits of nitrites and nitrates were 0.47 µg/L and 0.34 µg/L, respectively.

7. The concentrations of nitrites and nitrates in test samples 1#~3# were calculated by substituting each of the peak heights of nitrites and nitrates in the spectrograms of test samples 1#~3# into the regression equations obtained in step 6. The concentrations of nitrites and nitrates in test samples 1#~3# were obtained, as shown in Table 1.

TABLE 1

| Sample No. | Concentration of nitrites (µg/L) | | Concentration of nitrates (µg/L) | | Recovery rate (%) | |
|---|---|---|---|---|---|---|
| | Tagged | Measured | Tagged | Measured | Nitrites | Nitrates |
| 1# | 0 | 2.96 | 0 | 2.65 | | |
| | 0.50 | 3.48 | 2.00 | 4.70 | 103.1 | 102.3 |
| | 2.00 | 4.94 | 4.00 | 6.61 | 98.9 | 99.1 |
| 2# | 0 | 0 | 0 | 1.92 | | |
| | 0.10 | 0.10 | 1.00 | 2.93 | 102.4 | 100.6 |
| | 0.20 | 0.21 | 2.00 | 3.86 | 104.1 | 96.9 |
| 3# | 0 | 0 | 0 | 4.43 | | |
| | 0.10 | 0.10 | 3.00 | 7.50 | 101.9 | 102.3 |
| | 0.20 | 0.19 | 6.00 | 10.51 | 96.8 | 101.3 |

Example 6

Structure of Reduction Column and Preparation of Column Fillers

The reduction column in this example is substantially the same as that in Example 2, except that the inner diameter thereof is 4 mm, the column length thereof is 50 mm, and the column fillers are a mixture of copperized cadmium powders and polystyrene-divinylbenzene resin.

The column fillers were prepared as follows. 5 g cadmium powders having a particle size of 75~150 μm were added in a 100 mL beaker. 100 mL a mixed aqueous solution of copper sulfate and EDTA, in which the concentration of copper sulfate was 6.14 g/L and that of EDTA was 14.38 g/L, was then added slowly. The reaction was stirred for 10 min for copperization. After filtration, the resulting copperized cadmium powders were mixed with styrene-divinylbenzene resin having a particle size of 100~200 μm at a weight ratio of 1:1 to obtain the product.

Example 7

Figure 6:
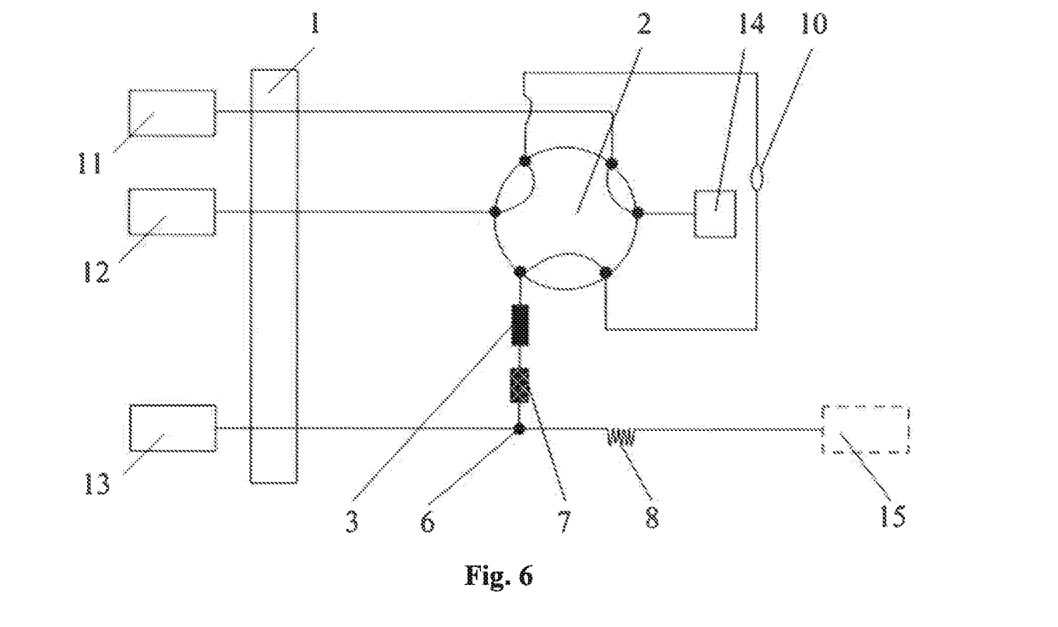
FIG. 6 is a structural schematic illustration of the apparatus according to the second aspect of the invention.

Apparatus (II) for Simultaneous Online Assay of Nitrites and Nitrates in Water Samples The structure of Apparatus (II) is shown in FIG. 6. It comprises a low pressure pump 1, a 6-way injection valve 2, a low pressure anion separation column 3, a mixer 6, a reduction column 7, a reactor 8, a sample loop 10, a sample vessel 11, an eluent vessel 12, a color developer solution vessel 13, and a waste liquid vessel 14. The reactor 8 and the low pressure anion separation column 3 are the same as those described in Example 3. The reduction column 7 is the one described in Example 6. Sample loop 10 is a polytetrafluoroethylene tube having a volume of 150 μL. The components of Apparatus (II) are assembled in the following way.

The sample vessel 11 is connected with a liquid inlet of the 6-way injection valve 2 via the low pressure pump 1. The eluent vessel 12 is connected with a liquid inlet of the 6-way injection valve 2 via the low pressure pump 1. The color developer solution vessel 13 is connected with an inlet of the mixer 6 via the low pressure pump 1. The liquid inlet and the liquid outlet of the sample loop 10 are connected with a liquid outlet and a liquid inlet of the 6-way injection valve 2, respectively. The liquid inlet of the low pressure anion separation column 3 is connected with a liquid outlet of the 6-way injection valve 2. The liquid inlet and the liquid outlet of the reduction column 7 are connected with the liquid outlet of the low pressure anion separation column 3 and the other inlet of the mixer 6, respectively. The outlet of the mixer 6 is connected with the inlet of the reactor 8. A liquid outlet of the 6-way injection valve 2 is connected with the waste liquid vessel 14. All connections are effected by ducts.

Example 8

Accuracy of Assay Using Apparatus (II)

A standard sample was assayed using Apparatus (II) described in Example 7 to evaluate the accuracy of the assay. The steps were as follows:

1. A mixed solution, as standard sample $S_2$, was prepared with deionized water, sodium nitrate, and sodium nitrite, having a nitrate concentration of 100 μg/L and a nitrite concentration of 50 μg/L.

2. Color developer solution R was prepared according to step 2 in Example 4.

3. A mixed aqueous solution having a sodium chloride concentration of 3.09 wt. % and an ammonium chloride concentration of 3.00 wt. % was prepared, as eluent E.

4. Assay was carried out and a spectrogram of the standard sample was mapped.

Figure 7:
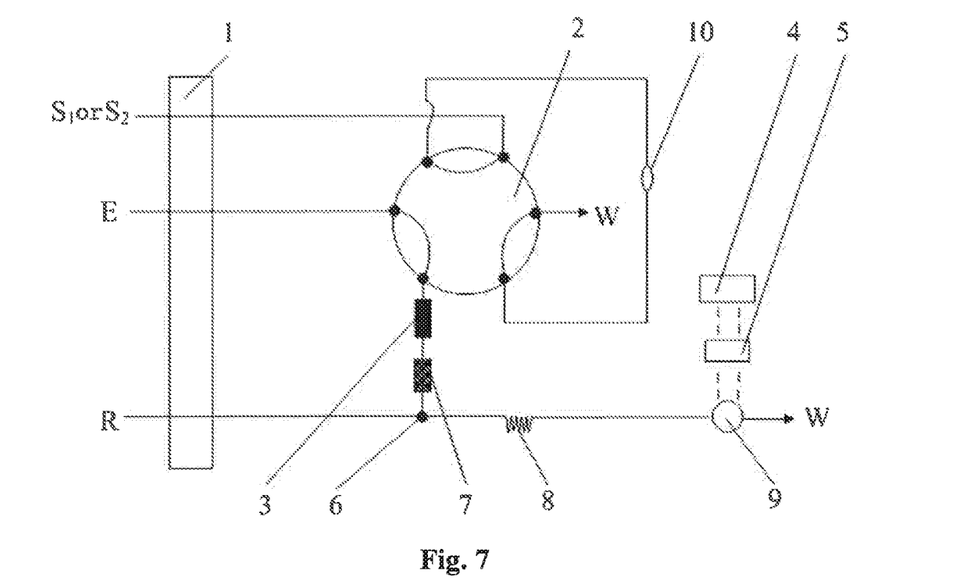
FIG. 7 is a schematic illustration of the flow path of the apparatus according to the second aspect of the invention in injection state when used in the method for simultaneous online assay of nitrites and nitrates in water samples.
Figure 8:
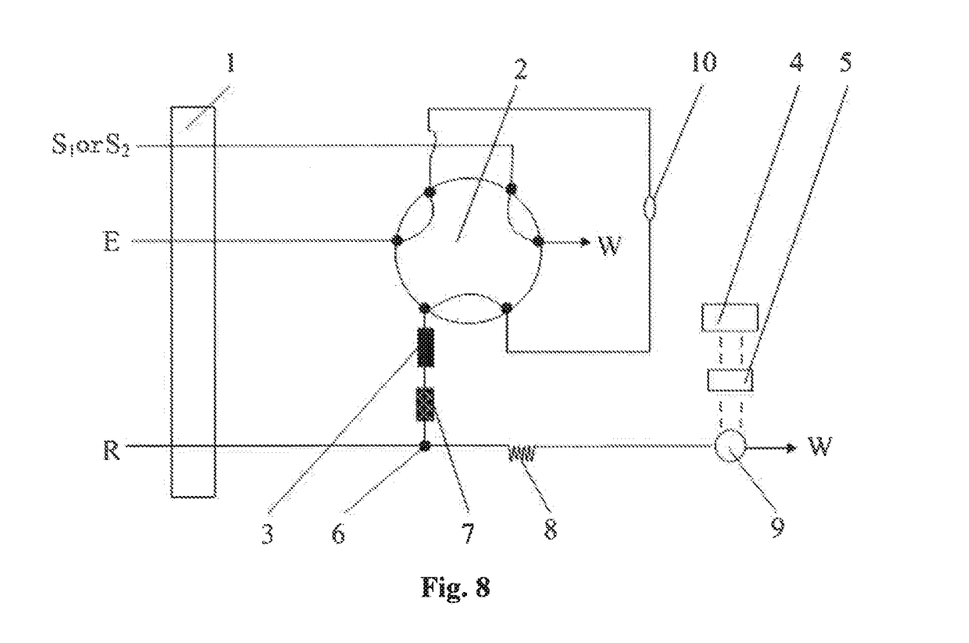
FIG. 8 is a schematic illustration of the flow path of the apparatus according to the second aspect of the invention in analytical state when used in the method for simultaneous online assay of nitrites and nitrates in water samples.

The assay was carried out using Apparatus (II) described in Example 7 (further comprising testing components 15, comprising an optical flow cell 9, an optical detector 5 and a computer system 4), and the flow paths as shown in FIG. 7 and FIG. 8 were employed. In the low pressure pump 1, the flow rate in the pump line of standard sample $S_2$ was 0.2~0.4 mL/min, the flow rate in the pump line of color developer solution R was 0.8~1.2 mL/min, the flow rate in the pump line of eluent E was 0.8~1.2 mL/min, and the working pressure was $2~3 \times 10^5$ Pa. The standard sample $S_2$, the eluent E and the color developer solution R were filled in the sample vessel 11, the eluent vessel 12, and the color developer solution vessel 13, respectively. The optical path of the optical flow cell 9 was 28 mm, and the detection wavelength of the optical detector 5 was 530 nm. The computer system 4 was a conventional computer installed with HW-2000 chromatography workstation (Shanghai Qianpu Software Company Ltd.).

The assay included the following steps:

(1) Baseline mapping. Apparatus (II) was set in injection state, and the flow path is shown in FIG. 7. The apparatus was turned on. Driven by the low pressure pump 1, eluent E entered the mixer 6 via the low pressure pump 1, the 6-way injection valve 2, the low pressure anion separation column 3, and the reduction column 7, color developer solution ft entered the mixer 6 via the low pressure pump 1, and they were mixed and formed a mixed solution in the mixer 6. The mixed solution entered the optical flow cell 9 via the reactor 8, and the signal produced by the optical detector 5 was transferred to the computer system 4 for processing to obtain a baseline. Simultaneously, standard sample $S_2$ entered the sample loop 10 via the low pressure pump 1 and the 6-way injection valve 2, and filled the sample loop 10. Excess standard sample $S_2$ was discharged into the waste liquid vessel 14 via a waste liquid outlet.

(2) Mapping of the spectrogram of the standard samples. Apparatus (II) was switched to analytical state, and the flow path is shown in FIG. 8. Driven by the low pressure pump 1, color developer solution R entered into the mixer 6 via the low pressure pump 1, and eluent E entered the sample loop 10 via the low pressure pump 1 and the 6-way injection valve 2 and brought the standard sample $S_2$ in the sample loop 10 to the low pressure anion separation column 3 via the 6-way injection valve 2. Driven by eluent E, the nitrites, which had low affinity to the column fillers, and the nitrates, which had high affinity to the column fillers, successively, flowed out of the low pressure anion separation column 3 and entered the reduction column 7. The nitrites entered the mixer 6 via the reduction column 7 and were mixed with color developer solution R, and then entered the reactor 8, where a color development reaction occurred to form a reaction solution. The nitrates were reduced to nitrites in the reduction column 7, the resulting nitrites entered the mixer 6 and were mixed with color developer solution R, and then entered the reactor 8, where a color development reaction occurred to form a reaction solution. The two reaction solutions entered, successively, the optical flow cell 9. The signal produced by the optical detector 5 was transferred to the computer system 4 for processing to obtain a spectrogram of the nitrites and the nitrates.

Figure 9:
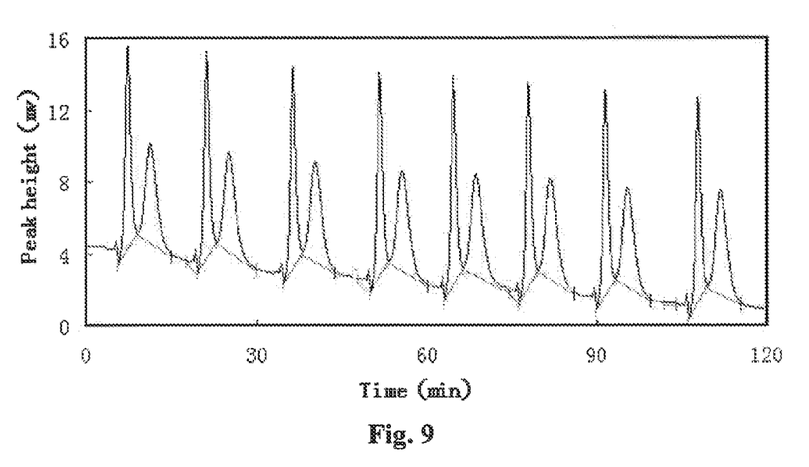
FIG. 9 is the spectrogram of accuracy of the standard sample obtained in Example 8.

The above steps (1) and (2) were repeated for 8 times, and a spectrogram as shown in FIG. 9 was obtained, wherein the relative standard deviation of the peak heights of nitrites and nitrates were 1.17% and 1.77%, respectively, demonstrating good accuracy of the assay of the invention.

Example 9

Assay of Water Samples Using Apparatus (II)

Water samples (seawater) were assayed using Apparatus (II) described in Example 7. A total of 2 samples (test sample 1# and test sample 2#) were assayed with the following steps:

1. Standard samples 1# to 5# were prepared with deionized water, sodium nitrate, and sodium nitrite, wherein standard sample 1# was an aqueous solution (3.09 wt. %) of sodium chloride; standard sample 2# was a mixed solution in which the concentrations of nitrites and nitrates were 5.0 µg/L and 20.0 µg/L, respectively; standard sample 3# was a mixed solution in which the concentrations of nitrites and nitrates were 10.0 µg/L and 100.0 µg/L, respectively; standard sample 4# was a mixed solution in which the concentrations of nitrites and nitrates were 30.0 µg/L and 500.0 µg/L, respectively; and standard sample 5# was a mixed solution in which the concentrations of nitrites and nitrates were 50.0 µg/L and 1000.0 µg/L, respectively.

2. Color developer solution R was prepared according to step 2 in Example 5.

3. A mixed aqueous solution having a sodium chloride concentration of 2.00 wt. % and an ammonium chloride concentration of 2.00 wt. % was prepared, as eluent E.

4. Assay was carried out and spectrograms of the standard samples were mapped.

The assay was carried out according to step 4 in Example 8, with steps (1) and (2) being performed using test sample 1#, test sample 2#, standard sample 1#, standard sample 2#, standard sample 3#, standard sample 4#, and standard sample 5#, respectively, in stead of standard sample $S_2$ in Example 8, obtaining a spectrogram of each of the test samples and the standard samples.

5. Working curves were plotted using the concentrations (µg/L) of standard samples 1#-5# on the X-axis, and the peak heights (mV) in the spectrograms of standard samples 1#-5# on the Y-axis. The resulting working curves of nitrites and nitrates were shown in FIG. 12 and FIG. 13, respectively.

Figure 12:
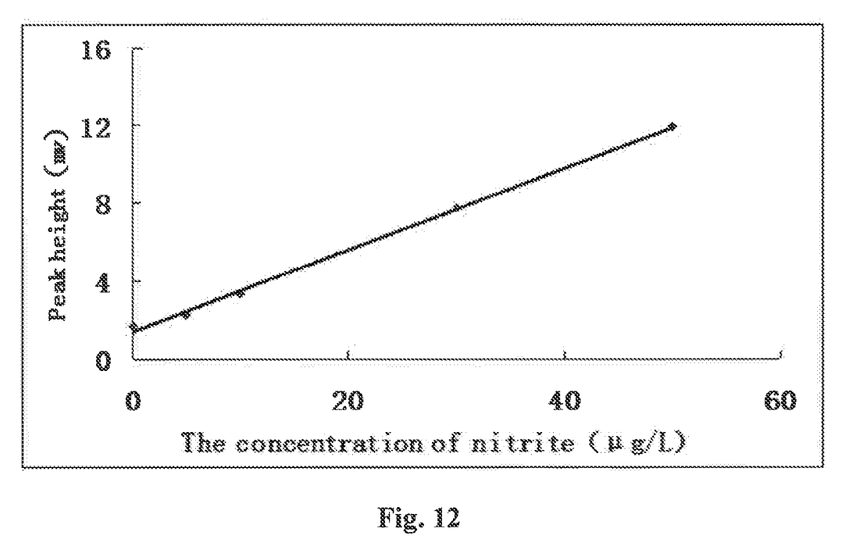
FIG. 12 is the working curve of nitrites obtained in Example 9.
Figure 13:
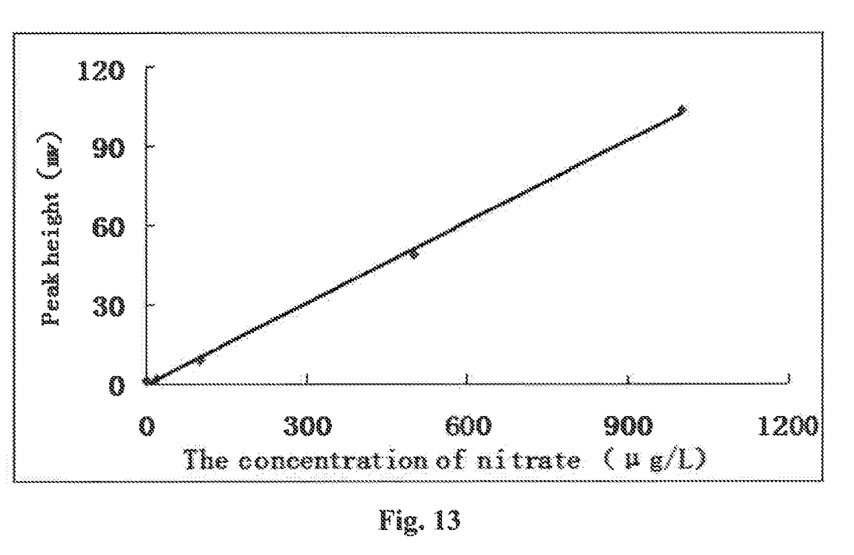
FIG. 13 is the working curve of nitrates obtained in Example 9.

6. Regression equations were established. The regression equation obtained from the working curve of nitrites as shown in FIG. 12 was H=0.2093C+1.4138, wherein H represented peak height (mV) and C represented concentration (µg/L) of nitrites in standard samples, and the correlation coefficient R was 0.999. The regression equation obtained from the working curve of nitrates as shown in FIG. 13 was H=0.1032C−0.6307, wherein H, C and R were as defined above for FIG. 12.

7. The concentrations of nitrites and nitrates in test samples 1# and 2# were calculated by substituting each of the peak heights of nitrites and nitrates in the spectrograms of test samples 1# and 2# into the regression equations obtained in step 6. The concentrations of nitrites and nitrates in test samples 1# and 2# were obtained, as shown in Table 2.

TABLE 2

| Sample No. | Concentration of nitrites (µg/L) | | Concentration of nitrates (µg/L) | | Recovery rate (%) | |
|---|---|---|---|---|---|---|
| | Tagged | Measured | Tagged | Measured | Nitrites | Nitrates |
| 1# | 0 | 21.4 | 0 | 81.7 | | |
| | 15.0 | 36.7 | 50.0 | 133.0 | 101.9 | 102.7 |
| | 20.0 | 41.5 | 100.0 | 182.5 | 100.3 | 100.8 |
| 2# | 0 | 5.67 | 0 | 141.8 | | |
| | 5.00 | 10.5 | 100.0 | 240.6 | 97.5 | 98.8 |
| | 10.0 | 15.8 | 200.0 | 346.2 | 101.3 | 102.2 |

What is claimed is:

1. An apparatus for simultaneous online assay of nitrites and nitrates in water samples, comprising a low pressure pump (1), a 6-way injection valve (2), a low pressure anion separation column (3), a mixer (6), a reduction column (7), a reactor (8), a sample vessel (11), an eluent vessel (12), a color developer solution vessel (13), and a waste liquid vessel (14), wherein the sample vessel (11) is connected with a liquid inlet of the 6-way injection valve (2) via the low pressure pump (1), the eluent vessel (12) is connected with a liquid inlet of the 6-way injection valve (2) via the low pressure pump (1), the color developer solution vessel (13) is connected with an inlet of the mixer (6) via the low pressure pump (1), the other inlet of the mixer (6) is connected with a liquid outlet of the 6-way injection valve (2), the liquid inlet and the liquid outlet of the low pressure anion separation column (3) are connected with a liquid outlet and a liquid inlet of the 6-way injection valve (2), respectively, the liquid inlet and the liquid outlet of the reduction column (7) are connected with the outlet of the mixer (6) and the inlet of the reactor (8), respectively, and a liquid outlet of the 6-way injection valve (2) is connected with the waste liquid vessel (14), wherein all connections are effected by ducts, and the reduction column (7) comprises a column body, filter membranes (7-4) located at the liquid inlet and the liquid outlet of the column body, and column fillers (7-3) in the inner cavity of the column body, wherein the column fillers (7-3) are copperized cadmium particles, or a mixture of copperized cadmium powders and polystyrene-divinylbenzene resin;

wherein the column fillers (7-3) are copperized cadmium particles, in which the cadmium particles have a particle size of 0.5-1.0 mm and the thickness of the copper layer is 0.05-0.1 mm.

2. An apparatus for simultaneous online assay of nitrites and nitrates in water samples, comprising a low pressure pump (1), a 6-way injection valve (2), a low pressure anion separation column (3), a mixer (6), a reduction column (7), a reactor (8), a sample vessel (11), an eluent vessel (12), a color developer solution vessel (13), and a waste liquid vessel (14), wherein the sample vessel (11) is connected with a liquid inlet of the 6-way injection valve (2) via the low pressure pump (1), the eluent vessel (12) is connected with a liquid inlet of the 6-way injection valve (2) via the low pressure pump (1), the color developer solution vessel (13) is connected with an inlet of the mixer (6) via the low pressure pump (1), the other inlet of the mixer (6) is connected with a liquid outlet of the 6-way injection valve (2), the liquid inlet and the liquid outlet of the low pressure anion separation column (3) are connected with a liquid outlet and a liquid inlet of the 6-way injection valve (2), respectively, the liquid inlet and the liquid outlet of the reduction column (7) are connected with the outlet of the mixer (6) and the inlet of the reactor (8), respectively, and a liquid outlet of the 6-way injection valve (2) is connected with the waste liquid vessel (14), wherein all connections are effected by ducts, and the reduction column (7) comprises a column body, filter membranes (7-4) located at the liquid inlet and the liquid outlet of the column body, and column fillers (7-3) in the inner cavity of the column body, wherein the column fillers (7-3) are copperized cadmium particles, or a mixture of copperized cadmium powders and polystyrene-divinylbenzene resin; wherein the column fillers (7-3) are a mixture of copperized cadmium powders and polystyrene-divinylbenzene resin in a weight ratio of 1:1-1:2.

3. The apparatus according to claim 1, further comprising an optical flow cell (9) downstream of the reactor (8), an optical detector (5) attached to the optical flow cell, and a computer system (4) connected to the optical detector.

4. An apparatus for simultaneous online assay of nitrites and nitrates in water samples, comprising a low pressure pump (1), a 6-way injection valve (2), a low pressure anion separation column (3), a mixer (6), a reduction column (7), a reactor (8), a sample loop (10), a sample vessel (11), an eluent vessel (12), a color developer solution vessel (13), and a waste liquid vessel (14), wherein the sample vessel (11) is connected with a liquid inlet of the 6-way injection valve (2) via the low pressure pump (1), the eluent vessel (12) is connected with a liquid inlet of the 6-way injection valve (2) via the low pressure pump (1), the color developer solution vessel (13) is connected with an inlet of the mixer (6) via the low pressure pump (1), the liquid inlet and the liquid outlet of the sample loop (10) are connected with a liquid outlet and a liquid inlet of the 6-way injection valve (2), respectively, the liquid inlet of the low pressure anion separation column (3) is connected with a liquid outlet of the 6-way injection valve (2), the liquid inlet and the liquid outlet of the reduction column (7) are connected with the liquid outlet of the low pressure anion separation column (3) and the other inlet of the mixer (6), respectively, the outlet of the mixer (6) is connected with the inlet of the reactor (8), and a liquid outlet of the 6-way injection valve (2) is connected with the waste liquid vessel (14), wherein all connections are effected by ducts, and the reduction column (7) comprises a column body, filter membranes (7-4) located at the liquid inlet and the liquid outlet of the column body, and column fillers (7-3) in the inner cavity of the column body, wherein the column fillers (7-3) are copperized cadmium particles, or a mixture of copperized cadmium powders and polystyrene-divinylbenzene resin;

wherein the column fillers (7-3) are copperized cadmium particles, in which the cadmium particles have a particle size of 0.5-1.0 mm and the thickness of copper layer is 0.05-0.1 mm.

5. An apparatus for simultaneous online assay of nitrites and nitrates in water samples, comprising a low pressure pump (1) a 6-way injection valve (2), a low pressure anion separation column (3), a mixer (6), a reduction column (7), a reactor (8), a sample loop (10), a sample vessel (11), an eluent vessel (12), a color developer solution vessel (13), and a waste liquid vessel (14), wherein the sample vessel (11) is connected with a liquid inlet of the 6-way injection valve (2) via the low pressure pump (1), the eluent vessel (12) is connected with a liquid inlet of the 6-way injection valve (2) via the low pressure pump (1), the color developer solution vessel (13) is connected with an inlet of the mixer (6) via the low pressure pump (1), the liquid inlet and the liquid outlet of the sample loop (10) are connected with a liquid outlet and a liquid inlet of the 6-way injection valve (2), respectively, the liquid inlet of the low pressure anion separation column (3) is connected with a liquid outlet of the 6-way injection valve (2), the liquid inlet and the liquid outlet of the reduction column (7) are connected with the liquid outlet of the low pressure anion separation column (3) and the other inlet of the mixer (6), respectively, the outlet of the mixer (6) is connected with the inlet of the reactor (8), and a liquid outlet of the 6-way injection valve (2) is connected with the waste liquid vessel (14), wherein all connections are effected by ducts, and the reduction column (7) comprises a column body, filter membranes (7-4) located at the liquid inlet and the liquid outlet of the column body, and column fillers (7-3) in the inner cavity of the column body, wherein the column fillers (7-3) are copperized cadmium particles, or a mixture of copperized cadmium powders and polystyrene-divinylbenzene resin; wherein the column fillers (7-3) are a mixture of copperized cadmium powders and polystyrene-divinylbenzene resin in a weight ratio of 1:1-1:2.

6. The apparatus according to claim 4, further comprising an optical flow cell (9) downstream of the reactor (8), an optical detector (5) attached to the optical flow cell, and a computer system (4) connected to the optical detector.

7. The apparatus according to claim 2, further comprising an optical flow cell (9) downstream of the reactor (8), an optical detector (5) attached to the optical flow cell, and a computer system (4) connected to the optical detector.

8. The apparatus according to claim 5, further comprising an optical flow cell (9) downstream of the reactor (8), an optical detector (5) attached to the optical flow cell, and a computer system (4) connected to the optical detector.

* * * * *